United States Patent [19]

Agback et al.

[11] Patent Number: 4,695,648

[45] Date of Patent: Sep. 22, 1987

[54] NOVEL ARYLACETIC ACID DERIVATIVES

[75] Inventors: Karl H. Agback; Tamara Agback, both of Upsala; Alf S. Nygren, Örbyhus, all of Sweden

[73] Assignee: Pharmacia AB, Upsala, Sweden

[21] Appl. No.: 775,058

[22] PCT Filed: Jan. 18, 1985

[86] PCT No.: PCT/SE85/00020

§ 371 Date: Aug. 29, 1985

§ 102(e) Date: Aug. 29, 1985

[87] PCT Pub. No.: WO85/03287

PCT Pub. Date: Aug. 1, 1985

[30] Foreign Application Priority Data

Jan. 19, 1984 [SE] Sweden ................................ 8400239

[51] Int. Cl.⁴ .............................................. C07C 69/76
[52] U.S. Cl. .................................... 560/053; 560/23; 560/52; 560/75; 562/435; 562/436; 562/460; 562/463; 562/478; 558/414; 558/423; 549/308; 549/310
[58] Field of Search .................. 560/53, 52, 75, 23; 562/478, 435, 436, 460, 463; 558/414, 423; 549/308, 310; 514/533, 545, 570

[56] References Cited

PUBLICATIONS

Chemical Abstract 140495p, vol. 75, 1971.
Chemical Abstract 140497r, vol. 75, 1971.
Chemical Abstract 58068e, vol. 78, 1973.

*Primary Examiner*—Paul J. Killos
*Attorney, Agent, or Firm*—Fred Philpitt

[57] ABSTRACT

A compound having a potentially inhibitory effect on 15-hydroxy-prostaglandin dehydrognase (PGDH) and having the formula

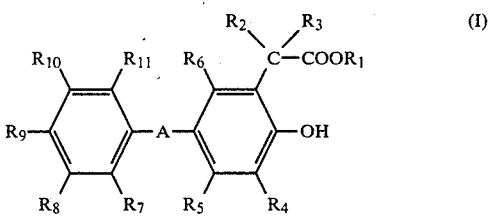

in which
$R_1$ and $R_2$ are hydrogen or lower alkyl;
$R_3$ is hydrogen, lower alkyl or substituted or unsubstituted phenyl;
$R_4$, $R_5$, and $R_6$ are hydrogen, halogen, lower alkyl, lower alkoxy, cyano, carboxy or nitro; at least one of the groups $R_4$ to $R_6$ being hydrogen;
$R_7$ to $R_{11}$ are hydrogen, halogen, cyano, lower alkyl, trifluoromethyl, lower alkoxy, hydroxy, lower acyl, lower alkoxycarbonyl, N,N,-diloweralkyl-aminocarbonyl or N,N-loweralkylene-aminocarbonyl; and $R_8$ and $R_{10}$ may in addition be carboxy; at least two of $R_7$ to $R_{11}$ always being hydrogen; and —A— is —CO—, —CH$_2$—CO—, —CH=CH—, —CH=CH—CO— or corresponding groups in which a hydrogen atom is replaced by a lower alkyl group.

The invention comprises also lactones of those compounds in which $R_1$ is hydrogen, and salts of those compounds which contain at least one carboxy group.

11 Claims, No Drawings

NOVEL ARYLACETIC ACID DERIVATIVES

The present invention is concerned with novel compounds having a potentially inhibitory effect on 15-hydroxy-prostaglandin dehydrogenase (PGDH). The invention is also concerned with the production of these novel compounds and with pharmaceutical compositions containing them.

The future potentialities of PGDH inhibitors, in respect of their usefulness in medicine, have not yet been fully explored. But it is a known fact that prostaglandins play a very important role in the body's regulating system, and for this reason any drugs interfering with either the synthesis or the degradation of prostaglandins may be potentially valuable medical tools. The so-called cytoprotective effect of prostaglandins is relatively well known in the context of ulcer therapies; but nevertheless prostaglandin administration has not been utilized to any major extent for therapeutic purposes because the prostaglandins administered will survive in vivo for only a very short time. A drug inhibiting the degradation of endogenous prostaglandins might conceivably be much more successful than prostaglandin administration.

Endogenous prostaglandins have a major role also in inflammatory processes. In the treatment of rheumatoid arthritis it is therefore at present quite a common practice to employ inhibitors of prostaglandin syntheses; but nowadays this is regarded as merely being a symptomatic treatment, and as a matter of fact certain prostaglandins are now believed to possibly have a very favorable effect. Thus in this context, too, the inhibition of PGDH dependent degradation may be potentially very valuable. Further potentially valuable medical fields of application for the present novel compounds are all those where prostaglandins may function as desirable controlling factors as e.g. in the case of circulatory disorders, cancer, fertility, cell regulation etc.

Examples of previously known compounds having an inhibitory effect on PHDH are such azo compounds as are set forth in EP-A-No. 21229.

These azo compounds, which have been employed earlier, have a number of drawbacks sufficiently severe to considerably impair the usefulness of these compounds in actual practical medicine. The most severe drawback is the fact that animals and humans will metabolically split the azo compounds reductively so as to form two aromatic amines. This type of metabolism occurs to a particularly large extent in (i) the liver and (ii) the large intestine where it is promoted due to the highly reducing conditions created by the intestinal microflora, i.e. the bacteria normally present in the intestine.

Such metabolism is apt to eliminate a considerable portion of the dose administered; already this in itself is a disadvantage. The greatest problem however arises due to the presence of the aforesaid aromatic amines such as for example aniline, chloroaniline etc. In view of the formation of these amines in vivo it is generally impossible to use the azo compounds in practical medicine; only in very special cases can the amine as formed in vivo be considered to be sufficiently harmless to permit a practical therapeutic use of the azo compounds. A lesser but non-negligable disadvantage is the strong coloring involved with these azo compounds—leading, in the most unfavorable cases, to clearly discernible color changes in the patient's skin, eyes etc., which is undesirable.

It is an object of the present invention to provide improved PGDH inhibitors and methods for their production. Further objects are to provide improved pharmaceutical compositions and treating methods involving such inhibitors.

The novel compounds have the following structure:

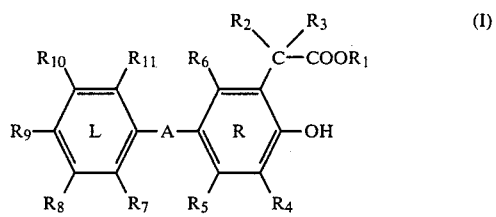

$R_1$ and $R_2$ are hydrogen or lower alkyl, preferably $R_2$ is hydrogen;

$R_3$ is hydrogen, lower alkyl or substituted or unsubstituted phenyl;

$R_4$, $R_5$ and $R_6$ are hydrogen, halogen, lower alkyl, lower alkoxy, cyano, carboxy or nitro; at least one of the groups $R_4$ to $R_6$ being hydrogen;

$R_7$ to $R_{11}$ are hydrogen, halogen, cyano, lower alkyl, trifluoromethyl, lower alkoxy, hydroxy, lower acyl, lower alkoxycarbonyl, N,N-diloweralkyl-aminocarbonyl or N,N,-loweralkylene-aminocarbonyl; and $R_8$ to $R_{10}$ may in addition be carboxy; at least two of $R_7$ to $R_{11}$ always being hydrogen, preferably $R_7$ and $R_{11}$ are hydrogen, halogen, cyano, lower alkyl, trifluoromethyl, lower alkoxy, hydroxy or lower acyl and —A— is —CO—, —CH$_2$—CO—, —CH=CH—, —CH=CH—CO— or corresponding groups in which a hydrogen atom is replaced by a lower alkyl group; the carbonyl group, if present, being attached to ring R of formula (I).

In the specification and claims, the terms "lower alkyl", "lower acyl" and "lower alkoxy" refer to groups containing preferably less than 6 carbon atoms.

The invention also comprises lactones of the compounds in which $R_1$ is hydrogen, and salts of the compounds containing at least one carboxy group, The preferred salts are pharmaceutically acceptable and therapeutically active.

Suitable salts are metal salts such as the sodium, potassium and calcium salt, or salts with organic amines such as e.g. diethanolamine, triethanolamine, N-methyl-glucamine, tris-hydroxymethyl-methylamine etc.

The novel compounds of this invention are virtually colorless and are not metabolized in a manner analogous to that of the azo compounds. Consequently the compounds of formula (I) are free from many of the disadvantages inherent in the azo compunds. Their PGDH-inhibiting effect is about as good as or better than that of the corresponding azo compounds.

A major advantage of the compounds according to the present invention resides in that they comprise groups greatly varying inter se in respect of their capacity of being absorbed from the gastrointestinal tract. This means that the invention comprises i.a. compounds which are rapidly and completely absorbed into the bloodstream - which is a valuable feature for obtaining a systemic effect. Other compounds, on the other hand, have a very low capacity for being absorbed and consequently will concentrate to the gastrointestinal tract; so this in turn means that some compounds of formula (I) may have a potential local activity against gastrointestinal disorders such as for instance gastric ulcer, Crohn's disease and ulcerative colitis.

The compunds according to the present invention may be produced by means of various combinations of known per se methods. For a general survey, these methods may be subdivided into 6 different general types; a specific method as chosen in actual practice will often be a combination of two or more of such general type methods.

General Type A

The first general type, A, is characterized in that a compound of the formula

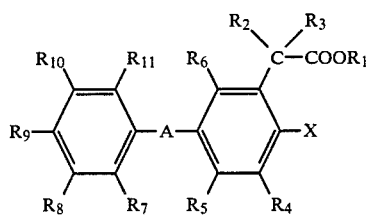

in which X is a group that can be replaced by OH and in which $R_1$ to $R_{11}$ and A have the same meanings as in formula (I) is treated so as to replace X by OH. Examples of the X group are amino, nitro, lower alkoxy, allyloxy, lower acyloxy, aroyloxy, lower alkylsulfonyloxy or arylsulfonyloxy. In case X is lower alkoxy the reaction is carried out by treatment with strongly acidic reagents such as e.g. strong mineral acids, for example sulfuric acid, hydrochloric acid or hydrobromic acid, and optionally in the presence of water. As an alternative to the use of mineral acids, the reaction may be performed in the presence of Lewis acids such as aluminum chloride, boron tribromide etc.

In case X is allyloxy the reaction is carried out in the same manner as in case X=alkoxy or, preferably, by means of isomerizing the double bond in the presence of water in an acidic medium to form the corresponding propenyl derivative which is rapidly hydrolyzed in the acidic medium. Such isomerization can be achieved by treatment with metal catalysts, e.g. palladium or platinum. In case X is lower acyloxy, aroyloxy, lower alkylsulfonyloxy or arylsulfonyloxy the reaction for replacement by OH is preferably performed by alkaline hydrolysis in water or in solvents mixed with and containing water. After the reaction the thus resultant reaction mixture is neutralized.

If X is $NH_2$ the reaction is most suitably carried out by means of diazotation followed by ordinary hydrolysis of the diazonium salt.

In case X is $NO_2$ the reaction is carried out by first reducing the $NO_2$ group to amino and then replacing the amino group by OH as set forth above.

General Type B

The second general type, B, is characterized in that a compound of the formula

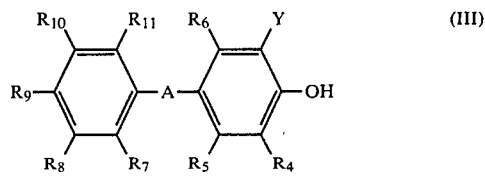

in which Y is a group replaceable by $—CR_2—R_3—COOR_1$ and in which $R_1$ to $R_{11}$ and A have the same meanings as in formula (I) is treated so as to replace Y by $—CR_2R_3—COOR_1$.

Examples of Y are H, $—CR_2R_3—CN$, $—CR_2R_3—CH=CH_2$, $—CO—COOR$ in which R is lower alkyl, $—C(SR)R_2—COOR_{12}$ in which R and $R_{12}$ are hydrogen or lower alkyl, $—C(OR)_2—CHX_1—R_2$ in which R is lower alkyl and $X_1$ is iodine, alkylsulfonyloxy or arylsulfonyloxy.

In case Y is H the reaction may be carried out via alkylation with $X_2—CR_2R_3—COOR_1$ where $X_2$ may be OH or halogen. If $X_2$ is halogen the reaction may be conducted under alkaline conditions in a manner such that the yield of C-alkylated product is maximized relatively to 0-alkylated product. Preferably the reaction is performed in the presence of Lewis acids such as $AlCl_3$, $SnCl_4$ or $TiCl_4$ under anhydrous conditions. In case $X_2$ is OH it is necessary that either (a) both $R_2$ and $R_3$ are lower alkyl or (b) $R_3$ is an optionally substituted phenyl while $R_2$ is hydrogen or lower alkyl. The reaction in case $X_2$ represents OH is preferably carried out in the presence of mineral acids, e.g. sulfuric acid.

In case Y is $—CR_2R_3—CN$ the reaction is carried out by means of acidic or alkaline hydrolysis in a known per se manner.

In case Y is $CR_2R_3—CH=CH_2$ the reaction is carried out by for instance oxidation with certain metal oxides (e.g. some oxides of transition metals, $KMnO_4$ or $CrO_3$), or with metaperiodate and e.g. $OsO_4$ or $RuO_4$ as catalyst.

In case Y is $—C(SR)R_2—COOR_{12}$ the reaction is a reduction carried out by e.g. treatment with Raney nickel or zinc in an acidic medium.

In case Y is $—C(OR)_2—CHX_1—R_3$ the reaction is performed in the presence of water and a weak base which neutralizes the acid formed. If $X_1$ is iodine it is advantageous to carry out the reaction by oxidizing with peroxides or other oxidants such as e.g. chlorine.

In case Y is $—CO—COOR$ the reaction is carried out by means of for example a catalytic reduction and hydrogenolysis.

General Type C

The third general type, C, is characterized by employing a compound of the formula

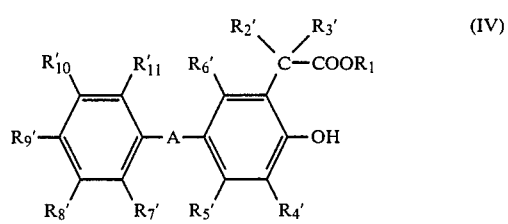

in which $R_1$ and A have the same meanings as in formula (I) and in which $R_2'$ to $R_{11}'$ have the same meanings as $R_2$ to $R_{11}$ of formula (I) except that at least one of the groups $R_2'$ to $R_{11}'$ is not identical with the corresponding group of the $R_2$ to $R_{11}$ series but is convertible to such a group by chemical reaction. If $R_3'$ is hydrogen conversion to a compound where $R_3$, is lower alkyl may be performed by means of alkylation in a known per se manner.

If $R_4'$, $R_5'$ and $R_6'$ are hydrogen, cyano, hydroxy or amino and chosen such that at least two of them are hydrogen the compound can be converted to a corresponding compound of formula (I) by means of halogenation in a known per se manner. If $R_4'$, $R_5'$ or $R_6'$ is cyano this group may be converted to carboxy (COOH) by means of hydrolysis in a known per se manner. In case one or two of the groups $R_4'$, $R_5'$ or $R_6'$ are hydroxy, that or those group(s) may be converted to alkoxy by alkylation in a known per se manner. If $R_4'$, $R_5'$ or $R_6'$ is amino it may be converted to halogen or cyano by diazotation followed by reaction with halogen salts or cyanide salts in a known per se manner.

Similarly $R_7'$ to $R_{11}'$ can be converted to a new group $R_7$ to $R_{11}$ in accordance with reaction types well known in themselves and corresponding to those set forth above.

General Type D

The fourth general type, D, is characterized by employing a compound of the formula

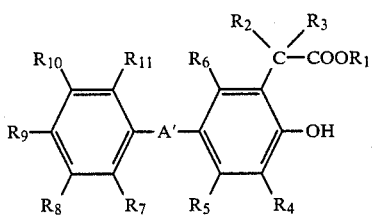

(V)

in which $R_1$ to $R_{11}$ have the same meanings as in formula (I) and A' is a group that is convertible to a corresponding group A of formula (I). A' may be for example —C(OR)2—, —CRX$_3$—CO—, —CR(OH)—CH$_2$—, —CHR—CH(OH)—, —CH$_2$—CRX$_3$—CO—, where R is hydrogen or lower alkyl, X$_3$ is OH; halogen or esterified alcoholic OH.

In case A' is —C(OR)2— the reaction is carried out by means of acidic hydrolysis with formation of the bridge —CO—.

In case A' is —CRX$_3$—CO— the reaction may be performed by means of reductive hydrogenolysis, preferably by means of catalytic hydrogenation specific for the C—X$_3$ bond.

In case A' is —CR(OH)—CH$_2$—, —CHR—CH(OH)— or —CH$_2$—CRX$_3$—CO— the reaction is carried out by means of eliminating H$_2$O or HX$_3$ by treatment with e.g. acids or alkaline reagents.

General Type E

The fifth general type, E, is characterized in that a compound of the formula

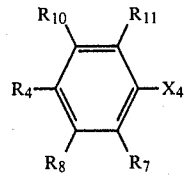

(VI)

in which $R_7$ to $R_{11}$ have the same meanings as in formula (I), is reacted with a compound of the formula

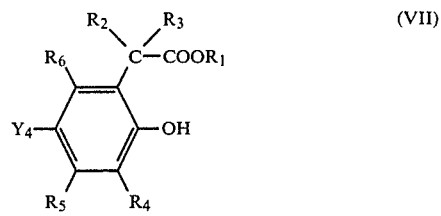

(VII)

in which $R_1$ to $R_6$ have the same meanings as in formula (I), in a manner such that X$_4$ and Y$_4$ react with each other so as to form the group —A—. Examples of the pair of groups X$_4$ and Y$_4$ are the following: —CO—X$_3$ and H or, resp., H and —CO—X$_3$ (X$_3$ being OH halogen); —CH2—CO—X$_3$ and H; —CR=P(C$_6$H$_5$)$_3$ and HCO— or —COR and (C$_6$H$_5$)$_3$P=CH—; —CHO and R—CH$_2$—CO.

If the reactions comprise acylation reactions these have to be carried out in the presence of suitable solvents, catalysts and reagents such as e.g. AlCl$_3$, SnCl$_4$, TiCl$_4$ or BF$_3$. For forming —CH=CR—CO— from —CHO and R—CH$_2$—CO— the reaction may be performed by means of e.g. acidic or alkaline catalysis in the presence of a solvent.

If —CR=CH— is to be formed from —CR=P(C$_6$H$_5$)$_3$ and HCO— or from —COR and (C$_6$H$_5$)$_3$P=CH— the reaction is carried out in a known per se manner.

General Type F

The sixth general type, F, is characterized in that a compound of formula (I) is converted to the corresponding lactone of the formula

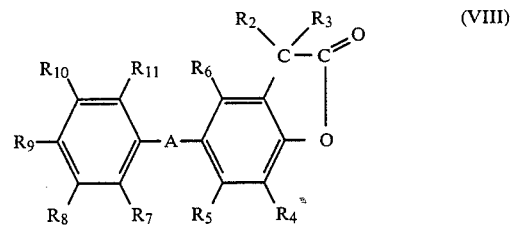

(VIII)

or that a lactone of formula (VIII) is converted to a compound of formula (I), or that $R_1$ is replaced by another $R_1$.

In case $R_1$ is hydrogen conversion to the lactone may be carried out in i simple manner by reaction with acids, if desired in the presence of water-withdrawing agents such as e.g. acetic anhydride or thionyl chloride or under other conditions by which water is removed such as for instance azeotropic distillation of water. In case $R_1$ is lower alkyl the reaction is performed by means of bases but is conducted carefully in order to prevent the lactone thus formed from being hydrolyzed to the corresponding acid.

The lactones according to the invention can readily be converted to corresponding acids by alkaline hydrolysis followed by acidification; or can readily be converted to corresponding esters by treatment with the corresponding alcohols in the presence of acidic catalysts, such as for example mineral acids.

If $R_1$ is hydrogen the compound may be converted to a corresponding ester in which $R_1$ is lower alkyl, this being achieved by esterfication in a known per se manner, If $R_1$ is lower alkyl the compound may be converted to the corresponding acid by means of alkaline hydrolysis followed by acidification in a known per se manner.

In producing a compound according to the invention an important advantage may often be gained if two or more of the methods belonging to the series of general types A to F are combined so that the reactions proceed simultaneously or in direct succession one after the other without isolation of intermediate products. For instance, it is often advantageous to react the compound

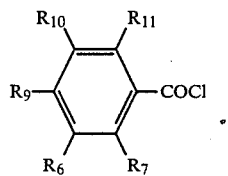

(IX)

with the compound

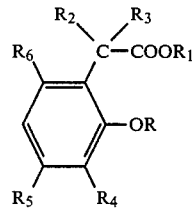

(X)

in which R and $R_1$ are lower alkyl, preferably methyl, and $R_2$ to $R_{11}$ have the same meanings as in formula (I) under the action of an excess of $AlCl_3$ so that the groups R and $R_1$ are split off simultaneously with or immediately after the acylation and/or during work-up. This will give a better yield than the yield obtained when that same type of reaction is carried out with e.g.

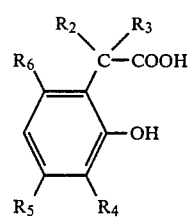

(XI)

or with the corresponding lactone, these compunds being much more sluggish in their reaction than the corresponding ether above (X).

Another example of simultaneous reactions is the conversion of the compound

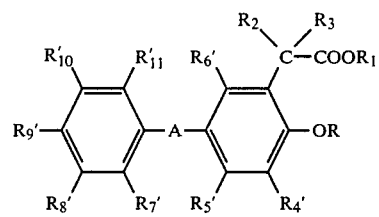

(XII)

in which $R_2$ and $R_3$ have the same meanings as in formula (I), R is lower alkyl, and one of the groups $R_4'$ to $R_{11}'$ is a hydrolyzable group such as e.g. cyanide, carboxylic acid ester or carboxylic acid amide.

The aforesaid hydrolyzable group selected from among $R_4'$ to $R_{11}'$ can be converted to a carboxy group by means of treatment with a strong mineral acid, while at the same time R and optionally $R_1$ are being replaced by hydrogen.

Still another example is the formation of the lactone concurrently with an acidic hydrolysis of a hydrolyzable group. Many such combinations will be illustrated in the numerous working examples below.

A compound of the invention containing at least one free carboxy group is readily convertible to corresponding salts by reaction with an equivalent amount of a suitable salt-forming reagent, such as for example sodium hydroxide, potassium hydroxide or a suitable organic amine, at a pH suitable for the compound in question and in the presence of a solvent. The salt may be prepared either as a solid by means of solvent removal in a known per se manner or directly in solution (if its solubility permits), preferably in aqueous solution, for pharmaceutical use directly in that form.

The novel pharmaceutical compositions according to the invention contain a therapeutically active amount of a compound of formula (I) or a lactone thereof or a salt of the compounds containing at least one carboxy group, if desired in combination with an organic or inorganic inert carrier material which is suitalbe for oral, rectal or parenteral administration. The pharmaceutical compositions may be solid, semisolid or liquid preparations, and optionally they may be sterilized and/or contain additional adjuvants. They can be prepared in a manner well known to persons skilled in the art: The active substance is mixed with the carrier material and optionally with additional adjuvants, and the mixture thus obtained is then converted to some sutiable galenic form. As for dosages, a general indication may be given by specifying for a person weighing 75 kg a daily dose within the range of from 1 to 1000 mg.

The novel treatment according to this invention for PGDH inhibition consists in administering to a mammal, including man, a pharmaceutical composition containing a therapeutically active amount of a compound of formula (I), a lactone thereof or a salt of the compounds containing at least one carboxy group.

The below working examples illustrate various embodiments of the invention without limiting its scope.

EXAMPLE 1

(a) Methyl 2-methoxy-benzeneacetate 500 g of 2-methoxy-benzeneacetic acid are dissolved in 4 l of methanol and 150 ml of sulfuric acid (d 1.84). The solution is boiled for 24 hours and poured onto ice water. The aqueous phase is extracted with chloroform which is then shaken against water and a solution of sodium hydrogen carbonate, whereupon the chloroform solution is evaporated.

(b) 5-Benzoyl-2-hydroxy-benzeneacetic acid 10.8 g of methyl 2-methoxy-benzeneacetate and 9 g of benzoyl chloride are dissolved in 65 ml of methylene chloride. During a 20 min. period, 25 g of aluminum chloride are added portionwise, with refluxing. The mixture is boiled for about 22 hours with stirring. After cooling to room temperatur the mixture is poured into water and extracted with about 300 ml of ether. After evaporation to dryness the residue is hydrolyzed with 200 ml of 1M sodium hydroxide +20 ml of ethanol by boiling for 1 hour. The pH is adjusted to 8 by addition of concentrated hydrochloric acid. After treatment with active carbon and filtration the solution is heated to about 70° C. and the pH is lowered to about 3 with hydrochloric acid to thereby cause the product to crystallize. After cooling the product is filtered off, washed with water and dried.

NMR spectrum and elemental analysis data are consistent with the structure of the title compound. Melting point 205° C.

EXAMPLE 2

(a) Methyl 2-hydroxy-benzeneacetate 250 g of 2-hydroxy-benzeneacetic acid are boiled for 24 hours with 2 l of methanol and 75 ml of sulfuric acid, d 1.84. The solution is poured onto ice water and extracted with chloroform. The chloroform solution is shaken against a solution of sodium hydrogen carbonate and water and is then dried with magnesium sulfate. The solution is evaporated, the residue being dissoved in methylene chloride and treated with active carbon. 400 ml of petroleum ether are added to the solution with gentle heating. The solution is cooled to −20° C. whereupon the crystals are filtered off and washed with petroleum ether.

(b) 5-Benzoyl-2-hydroxy-benzeneacetic acid 16.6 g of methyl-2-hydroxy-benzeneacetate and 14 g of benzoyl chloride are dissolved in 100 ml of nitrobenzene. 27 g of aluminum chloride are added portionwise during a period of about 10 minutes. The solution is stirred at 60° C. for 24 hours. After cooling, it is poured onto ice water and hydrochloric acid. The mixture is extracted with chloroform, and the chloroform phase is steam distilled. The distillation residue is leached with hot water, dissolved in chloroform and shaken against a solution of sodium hydrogen carbonate. The chloroform phase is evaporated, and the residue is boiled for 1 hour in 2 g of sodium hydroxide dissolved in 100 ml of water. 100 ml of methanol are added to the hot solution which is then acidified with formic acid. After cooling, the product is filtered off and dried.

NMR spectrum and elemental analysis data are consistent with the structure of the title compound. Melting point 205° C.

EXAMPLE 3

(a) 5-(3,5-Dimethyl-benzoyl)-2-methoxy-benzeneacetic acid 15 g of 3,5-dimethyl-benzoic acid, 200 ml of chloroform, 10 ml of thionyl chloride and 1 ml of dimethyl formamide are boiled until no more HCl is evolved. The solution is concentrated and mixed with 16 g of methyl 2-methoxy-benzeneacetate and 100 ml of nitrobenzene. During a 15 min. period 39 g of aluminum chloride are added in portions, and the flask is maintained at about 55° C. for 18 hours. The solution is poured onto ice-cold hydrochloric acid and extracted with chloroform.

The chloroform phase is washed with water and is steam distilled, the residue being hydrolyzed in 200 ml of 1M sodium hydroxide and 20 ml of ethanol. The pH is adjusted to about 7 and the solution is shaken against chloroform. It is then concentrated by evaporation, and upon cooling 23,5 g of crystals precipitate. These crystals are dissolved in 400 ml of water and 100 ml of ethanol; acetic acid is added to thereby cause the acid to crystallize.

NMR spectrum and elemental analysis data are consistent with the structure of the title compound (b) 5-(3,5-Dimethyl-benzoyl)-2-hydroxy-benzeneacetic acid 10 g of 5-(3,5-dimethylbenzoyl)-2-methoxy-benzeneacetic acid, 40 ml of hydrobromic acid (40 % w/v in acetic acid), 15 ml of water and 2 ml of hydroiodic acid are refluxed for 24 hours. After cooling, the solution is poured onto water. The precipitate is filtered off and is boiled for 1 hour in 100 ml of 2M sodium hydroxide solution, whereupon this is diluted with 600 ml of water and 100 ml of ethanol. The pH is adjusted to about 7, and the solution is treated with active carbon and heated to its boiling temperature. Acetic acid is added. Crystals precipitating from the solution are filtered off, dissolved and treated with active carbon in acetic acid. When water is added to the solution the product crystallizes; it is then recrystallized from acetic acid.

NMR spectrum and elemental analysis data are consistent with the structure of the title compound. Melting point 242° C.

EXAMPLE 4

(a) 2-Phenyl-6-(2-phenyl-1-ethenyl)-4H-1,3,2-benzodioxaborinan 19.6 g of 4-(2-phenyl-1-ethenyl)-phenol, 14.6 g of benzeneboronic acid, 3.8 g of propionic acid and 100 ml of toluene are refluxed employing a water separator.

During a 1.5 hour period 12.0 g of paraformaldehyde are added in small portions. The mixture is then boiled for an additional hour. After cooling to room temperatur and addition of 100 ml of ether the product thus crystallized is filtered off and washed with ether.

(b) 2-Hydroxy-5-(2-phenyl-1-ethenyl)-benzenemethanol 21.6 g of 2-phenyl-6-(2-phenyl-1-ethenyl)-4H-1,3,2-benzodioxaborinan are suspended in 130 ml of tetrahydrofuran. During a period of about 10 min. 32.5 ml of 30 % w/w hydrogen peroxide are added portionwise with agitation and cooling to room temperature. The reaction mixture is left standing for 20 minutes and then poured into ice water, whereupon the product thus precipitated is filtered off and washed with water.

(c) 2-Hydroxy-5-(2-phenyl-1-ethenyl)-benzeneacetic acid 9.1 g of 2-hydroxy-5-(2-phenyl-1-ethenyl)-benzenemethanol and 3.15 g of potassium cyanide are heated for 24 hours in 120 ml of dimethyl formamide to 120° C. 20 ml of water are added, and the pH is adjusted to about 10 by means of sodium hydroxide. The solution is evaporated to dryness. The residue is dissolved in 50 ml of water. The solution is neutralized with acetic acid and extracted several times with ether. After having been washed with water the ether phase is evaporated to dryness.

The residue is hydrolyzed in 10 ml of water and 7 ml of concentrated sulfuric acid by boiling for 6 hours. The solution is diluted with water and extracted with ether. After reextraction to alkaline aqueous solution, this solution is acidified and extracted back to ether. After drying and concentration the product compound is purified by repeated reprecipitations from alkali with acid and recrystallization from acetone and petroleum ether.

NMR spectrum and elemental analysis data are consistent with the structure of the title compound. Melting point 202° C.

EXAMPLE 5

2-Hydroxy-5-(4-chlorobenzoyl)-benzeneacetic acid 17.5 g of 4-chlorobenzoyl chloride and 16.6 g of methyl 2-hydroxy-benzeneacetate are dissolved in 100 ml of nitrobenzene. 27 g of aluminum chloride are added in portions during a period of about 20 minutes. The solution is maintained at 60° C. for 16 hours, whereupon it is poured onto ice - hydrochloric acid. The mixture is extracted with chloroform, and the chloroform phase is steam distilled. The distillation residue is dissolved in chloroform, treated with active carbon and shaken against a solution of sodium hydrogen carbonate. The chloroform solution is evaporated, the remaining oil is stirred with petroleum ether - benzene, and the crystals thus formed are filtered off. The crystals are hydrolyzed by boiling for 1 hour with 4 g sodium hydroxide in 100 ml of water, and hydrochloric acid is added dropwise until crystals start to precipitate. After cooling the product is filtered off and dried.

NMR spectrum and elemental analysis data are consistent with the structure of the title compound. Melting point 250° C.

EXAMPLE 6

5-(4-Cyanobenzoyl)-2-hydroxy-benzeneacetic acid 14.7 g of 4-cyanobenzoic acid, 100 ml of chloroform, 10 ml of thionyl chloride and 0.25 ml of dimethyl formamide are boiled for 6 hours. The solution is evaporated, the residue being dissolved in 100 ml nitrobenzene, 16.6 g of methyl 2-hydroxy-benzene-acetate are added and then 40 g of aluminum chloride in portions during a period of about 20 min. The solution is maintained at 50° C. for 8 hours and is then poured onto ice - hydrochloric acid. The mixture is extracted with ether and the ether phase is evaporated. The oil is subjected to steam distillation and the residue is extracted with chloroform, whereupon the chloroform solution is dried with magnesium sulfate and treated with active carbon. The chlorofrm solution is evaporated; the residue is dissolved in about 50 ml of ethanol and is hydrolyzed in 100 ml solution of potassium hydroxide at pH 10. The resultant solution is diluted to 0.5 l and acidified with formic acid. The product crystallizes and is filtered off and dried.

NMR spectrum and elemental analysis data are consistent with the structure of the title compound. Melting point 218° C.

EXAMPLE 7

2-Hydroxy-5-(4-carboxybenzoyl)-benzeneacetic acid 2 g of 5-(4-cyanobenzoyl)-2-hydroxy-benzeneacetic acid are boiled for 24 hours in 20 ml of acetic acid, 10 ml of water and 10 ml of sulfuric acid. The solution is cooled to room temperature. The precipitate is filtered off and washed with water.

The precipitate is boiled for 18 hours in 1M potassium hydroxide solution. The solution is acidified with formic acid and cooled. The product that is thus crystallized out is filtered off, washed with water and dried.

NMR spectrum and elemental analysis data are consistent with the structure of the title compound. Melting point >260 C.

EXAMPLE 8

(a) Methyl 5-(4-cyanobenzoyl)-2-methoxy-benzeneacetate 10 g of 4-cyanobenzoic acid, 8 ml of thionyl chloride, 0.5 ml of dimethyl formamide and 100 ml of chloroform are boiled for a period of 16 hours and then evaporated.

35 g of aluminum chloride are dissolved in 80 ml of nitrobenzene. To this are added the acid chloride and 12.2 g of methyl 2-methoxybenzeneacetate dissolved in 20 ml of nitrobenzene. The solution is maintained at 60° C. for 24 hours, whereupon it is poured onto ice water and extracted with methylene chloride. The methylene chloride phase is shaken against diluted hydrochloric acid and water. It is then concentrated and diluted with petroleum ether. Crystals are filtered off and recrystallized from ethanol.

(b) 2-Hydroxy-5-(4-carboxybenzoyl)-benzeneacetic acid 10 g of methyl 5-(4-cyanobenzoyl)-2-methoxy-benzene-acetate are boiled for 24 hours in 100 ml of 40 % hydrobromic acid in acetic acid, 30 ml of water and 2 ml of hydroiodic acid. The solution is poured into water, the precipitate is filtered off, and the mother liquor is extracted with ethyl acetate, evaporated and pooled with the precipitate. The product is boiled for 30 min. in 0,5M sodium hydroxide solution, the pH is adjusted to about 6 with acetic acid, and the solution is treated with active carbon. It is then heated to about 70° C. and formic acid is added to thus initiate crystallization of the product, and the solution is then cooled. The product is filtered off, washed with water and dried.

NMR spectrum and elemental analysis data are consistent with the structure of the title compound. Melting point >260° C.

EXAMPLE 9

5-Benzoyl-3-bromo-2-hydroxy-benzeneacetic acid 13 g of 5-benzoyl-2-hydroxy-benzeneacetic acid and 5 g sodium acetate are dissolved in 150 ml of tetrahydrofuran. During a period of about 1 hour 10 g of bromine dissolved in 50 ml of tetrahydrofuran are added dropwise. The solution is evaporated, whereupon the residue is dissolved in a little methanol. The methanolic solution is acidified with sulfuric acid and filtered. The solution is diluted with 150 ml of methanol. 20 ml of sulfuric acid are added, whereupon the solution is boiled for 18 hours. It is then poured onto ice water, extracted with benzene and recrystallized from benzene-isooctane. The product is recrystallized twice from methanol-water and hydrolyzed in 1M sodium hydroxide solution. The resultant solution is acidified with hydrochloric acid, extracted with chloroform, dried with magnesium sulfate and evaporated. The residue is recrystallized from benzene-isooctane. The product is filtered off and dried.

NMR spectrum and elemental analysis data are consistent with the structure of the title compound. Melting point 132° C.

EXAMPLE 10

5-(2-Fluorobenzoyl)-2-hydroxy-benzeneacetic acid 14 g of 2-fluorobenzoic acid, 100 ml of chloroform, 10 ml of thionyl chloride and 1 ml of dimethyl formamide are boiled for 6 hours. The solution is concentrated and mixed with 18 g of methyl 2-methoxybenzene-acetate and 50 ml of methylene chloride, the resulting mixture then being added dropwise to a suspension of 50 g aluminium chloride in 150 ml methylene chloride, and this is followed by boiling for 6 hours. The solution is then poured onto ice water, extracted with chloroform, dried with magnesium sulfate, treated with active carbon and evaporated. The residue is recrystallized from benzeneisooctane. The product is hydrolyzed in 300 ml of sodium hydroxide solution, and the hot solution is acidified with acetic acid. The product starts to crystallize, the solution is cooled, and the product is filtered off.

NMR spectrum and elemental analysis data are consistent with the structure of the title compound. Melting point 102° C.

EXAMPLE 11

5-(2,4-Dichlorobenzoyl)-2-hydroxy-benzeneacetic acid

This synthesis is carried out in a manner analogous to that of Example 10.

NMR spectrum and elemental analysis data are consistent with the structure of the title compound. Melting poing 226° C.

EXAMPLE 12

5-(3-Fluorobenzoyl)-2-hydroxy-benzeneacetic acid

This synthesis is carried out in a manner analogous to that of Example 10.

NMR spectrum and elemental analysis data are consistent with the structure of the title compound. Melting point 171° C.

EXAMPLE 13

5-Benzoyl-2-hydroxy-3-chloro-benzeneacetic acid 11.3 g of methyl 5-benzoyl-2-hydroxy-benzeneacetate, 5.7 g of N-chlorosuccinimide and 100 ml of chloroform are boiled for 18 hours. The suspension is evaporated, dissolved in benzene and shaken against water. The benzene solution is dried and evaporated. The residue is recrystallized from benzene - isooctane. The product is boiled for 1 hour in sodium hydroxide solution, whereupon the solution thus obtained is acidified with hydrochloric acid. The solution is then cooled, and the product which has formed is filtered off and dried.

NMR spectrum and elemental analysis data are consistent with the structure of the title compound. Melting point 131° C.

EXAMPLE 14

5-(2-Phenylacetyl)-2-hydroxy-benzeneacetic acid 16.6 g of methyl 2-hydroxy-benzeneacetate and 15.4 g of phenylacetyl chloride are dissolved in 100 ml of nitrobenzene. 27 g of aluminum chloride are added portionwise at room temperatur, whereupon the solution is maintained at 60° C. for 8 hours. It is then poured onto ice-hydrochloric acid and extracted with chloroform. The chloroform solution is steam distilled, and the residue from that distillation is hydrolyzed in boiling sodium hydroxide solution. The pH is adjusted to 7 and the solution is extracted with chloroform.

The aqueous phase is acidified with hydrochloric acid whereafter the crystals thus formed are filtered off and dried. The product is recrystallized from ethyl methyl ketone - chloroform.

NMR spectrum and elemental analysis data are consistent with the structure of the title compound. Melting point 198° C.

EXAMPLE 15

(a) Methyl 5-(2-(4-cyanophenyl)-acetyl)-2-methoxybenzeneacetate 18.2 g of 4-cyano-benzeneacetic acid, 12 ml of thionyl chloride, 100 ml of chloroform and 0.5 ml of dimethyl formamide are boiled for 4 hours. The solution is evaporated, the residue being dissolved in 20.3 g of methyl 2-methoxy-benzeneacetate and 50 ml of methylene chloride. This solution is added dropwise to a solution of 60 ml of tin chloride in 250 ml of methylene chloride. The solution is boiled for 18 hours, poured onto ice water and extracted with chloroform. The chloroform phase is dried with magnesium sulfate, treated with active carbon and evaporated. The residue is recrystallized twice from ethanol.

(b) 2-Hydroxy-5-(2-(4-carboxyphenyl)-acetyl)-benzeneacetic acid

This synthesis is carried out in a manner analogous to that of Example 8.

NMR spectrum and elemental analysis data are consistent with the structure of the title compound. Melting point >260° C.

EXAMPLE 16

(a) Methyl 5-acetyl-2-hydroxy-benzeneacetate 36 g of methyl 2-methoxy-benzeneacetate and 15.7 g of acetyl chloride are dissolved in 100 ml of methylene chloride, the resultant solution then being added dropwise to a suspension of 100 g of aluminum chloride in 300 ml methylene chloride. The solution is boiled for 5 hours, poured onto ice water and filtered. The crystals are washed with water and methylene chloride.

(b)
5-(3-Phenyl-1-oxo-2-propenyl)-2-hydroxy-benzeneacetic acid 10.4 g of methyl 5-acetyl-2-hydroxy-benzeneacetate, 5.3 g of benzaldehyde, 50 ml of 5M sodium hydroxide and 50 ml of ethanol are agitated for 4 hours in an ice bath and for 20 hours at room temperatur. The solution is diluted with 150 ml of water, and acetic acid is added dropwise. The precipitate is filtered off and dried. It is recrystallized from ethyl methyl ketone - benzene and dried.

NMR spectrum and elemental analysis data are consistent with the structure of the title compound. Melting point 198° C.

EXAMPLE 17

2-Hydroxy-5-(3-(4-carboxyphenyl)-1-oxo-2-propenyl)-benzeneacetic acid

This synthesis is carried out in a manner analogous to that of Example 16 (b).

NMR spectrum and elemental analysis data are consistent with the structure of the title compound. Melting point >260° C.

EXAMPLE 18

(a) Methyl 5-(3-cyanobenzoyl)-2-methoxybenzeneacetate 14.7 g of 3-cyanobenzoic acid, 40 ml of chloroform, 10 ml of thionyl chloride and 0.2 ml of dimethyl formamide are boiled for 18 hours.

The solution is concentrated and then mixed with 7.3 g of methyl 2-methoxy-benzeneacetate and 20 ml of methylene chloride. The resultant solution is added to a solution of 24 ml of stannic chloride in 100 ml of methylene chloride, and the whole is boiled for 48 hours.

The solution is poured onto ice water, extracted with chloroform, treated with active carbon and evaporated. The residue is leached with a little ethanol and recrystallized from methanol - water.

(b) 2-Hydroxy-5-(3-carboxybenzoyl)-benzeneacetic acid

This synthesis is carried out in a manner analogous to that of Example 8.

NMR spectrum and elemental analysis data are consistent with the structure of the title compound. Melting point >260° C.

EXAMPLE 19

Methyl 2-hydroxy-5-(2-chlorobenzoyl)-benzeneacetate 15.6 g of 2-chlorobenzoic acid, 10 ml of thionyl chloride, 150 ml of methylene chloride and 0.5 ml of dimethyl formamide are boiled until evolution of hydrogen chloride has ceased. The solution is evaporated, and the residue is dissolved in 18 g of methyl 2-methoxy-benzeneacetate and 50 ml of methylene chloride. The solution is added dropwise to a suspension of 50 g of aluminum chloride in 200 ml of methylene chloride and boiled for 16 hours. The solution is poured onto ice water, extracted with chloroform, dried and treated with active carbon. It is then evaporated, the residue being dissolved in benzene - petroleum ether and treated with active carbon. More petroleum ether is added to precipitate crystals.

NMR spectrum and elemental analysis data are consistent with the structure of the title compound. Melting point 119° C.

EXAMPLE 20

Methyl-5-(4-fluorobenzoyl)-2-hydroxy-benzeneacetate

This synthesis is carried out in a manner analogous to that of Example 19.

NMR spectrum and elemental analysis data are consistent with the structure of the title compound. Melting point 173° C.

EXAMPLE 21

5-(4-Fluorobenzoyl)-2-hydroxy-benzeneacetic acid 15 g of methyl 5-(4-fluorobenzoyl)-2-hydroxy-benzeneacetate are boiled for 15 minutes in 300 ml of 0.5M sodium hydroxide solution and 10 ml of ethanol. The pH is adjusted to about 7 with hydrochloric acid, and the hot solution is acidified with acetic acid. The solution is cooled to about 40° C. Crystals are filtered off and washed with water.

NMR spectrum and elemental analysis data are consistent with the structure of the title compound. Melting point 218° C.

EXAMPLE 22

(a) Methyl 5-(2-(2-fluoro-6-chlorophenyl)-acetyl)-2-hydroxy-benzeneacetate

This synthesis is carried out in a manner analogous to that of Example 19.

(b) 5-(2-(2-Fluoro-6-chlorophenyl)-acetyl)-2-hydroxy-benzeneacetic acid

This synthesis is carried out in a manner analogous to that of Example 21.

NMR spectrum and elemental analysis data are consistent with the structure of the title compound. Melting point 240° C.

EXAMPLE 23

(a) 5-(2-(1-Chlorophenyl)-acetyl)-2-methoxy-benzeneacetic acid 17 g of 2-chloro-benzeneacetic acid, 10 ml of thionyl chloride, 0.5 ml of dimethyl formamide and 150 ml of methylene chloride are boiled for 6 hours. The solution is evaporated, and the residue is dissolved in 18 g of methyl 2-methoxy-benzeneacetate and 50 ml of methylene chloride. The resultant solution is added dropwise to a solution of 50 ml tin chloride in 250 ml methylene chloride. The solution is boiled for 24 hours, poured onto ice water, extracted with chloroform, dried and treated with active carbon. The chloroform solution is evaporated and the residue is recrystallized from ethanol. Hydrolysis of the crystals in 200 ml of 1M sodium hydroxide is followed by dilution with water and 50 ml ethanol to a volume of about 300 ml, whereupon the solution is acidified with acetic acid while boiling. It is then cooled, and the crystals are filtered off.

(b) 2-Hydroxy-5-(2-(2-chlorophenyl)-acetyl)-benzeneacetic acid

This syntesis is carried out in a manner analogous to that of Example 3 (b).

NMR spectrum and elemental analysis data are consistent with the structure of the title compound. Melting point 230° C.

EXAMPLE 24

5-(3-(4-Fluorophenyl)-1-oxo-2-propenyl)-2-hydroxybenzeneacetic acid

This synthesis is carried out in a manner analogous to that of Example 16 (b).

NMR spectrum and elemental analysis data are consistent with the structure of the title compound. Melting point 212° C.

EXAMPLE 25

(a) 5-(2,6-Difluorobenzoyl)-2-methoxy-benzeneacetic acid

This synthesis is carried out in a manner analogous to that of Example 23 (a).

NMR spectrum and elemental analysis data are consistent with the structure of the title compound. Melting point 187° C.

(b) 5-(2,6-Difluorobenzoyl)-2-hydroxy-benzeneacetic acid

This synthesis is carried out in a manner analogous to that of Example 3 (b).

NMR spectrum and elemental analysis data are consistent with the structure of the title compound. Melting point 120° C.

EXAMPLE 26

5-(2-Chlorobenzoyl)-2-hydroxy-benzeneacetic acid

This synthesis is carried out in a manner analogous to that of Example 21. NMR spectrum and elemental analysis data are consistent with the structure of the title compound. Melting point 148° C.

EXAMPLE 27

(a) Methyl 5-benzoyl-2-methoxy-α,α-dimethylbenzeneacetate 13 g of 5-benzoyl-2-methoxy-benzeneacetic acid are dissolved in 150 ml of dimethyl formamide. 10 g of sodium hydride in 50 ml of dimethyl formamide are added. The solution is cooled in ice, and 30 ml of methyl iodide are added in portions. The solution is allowed to warm to room temperatur after a period of about 6 hours, the last portion of methyl iodide being then added after another 16 hours. Methanol is then added and the solution is poured onto ice water - hydrochloric acid. It is extracted with chloroform and the thus resultant solution is evaporated. The residue is boiled for 2 hours in a 50 % ethanol 1M sodium hydroxide solution. The resultant solution is shaken with chloroform; the chloroform phase is dried with magnesium sulfate and evaporated. The residue is stirred with petroleum ether, the supernatant is removed by decantation, and the remaining portion is recrystallized from petroleum ether - benzene.

(b) 5-Benzoyl-2-hydroxy-α,α-dimethyl-benzeneacetic acid

This synthesis is carried out in a manner analogous to that of Example 3 (b).

NMR spectrum and elemental analysis data are consistent with the structure of the title compound. Melting point 207° C.

EXAMPLE 28

5-(3-(2,4-Dichlorophenyl)-1-oxo-2-propenyl)-2-hydroxybenzeneacetic acid

This synthesis is carried out in a manner analogous to that of Example 16 (b).

NMR spectrum and elemental analysis data are consistent with the structure of the title compound. Melting point 232° C.

EXAMPLE 29

5-(3-(4-(1-Methyl-ethyl)-phenyl)-1-oxo-2-propenyl)-2-hydroxy-benzeneacetic acid

This synthesis is carried out in a manner analogous to that of Example 16 (b).

NMR spectrum and elemental analysis data are consistent with the structure of the title compound. Melting point 228° C.

EXAMPLE 30

5-(3-(4-Methoxyphenyl)-1-oxo-2-propenyl)-2-hydroxybenzeneacetic acid

This synthesis is carried out in a manner analogous to that of Example 16 (b).

NMR spectrum and elemental analysis data are consistent with the structure of the title compound. Melting point 247° C.

EXAMPLE 31

5-(3-(4-Chlorophenyl)-1-oxo-2-propenyl)-2-hydroxybenzeneacetic acid

This synthesis is carried out in a manner analogous to that of Example 16 (b).

NMR spectrum and elemental analysis data are consistent with the structure of the title compound. Melting point 244° C.

EXAMPLE 32

5-(4-Acetylbenzoyl)-2-hydroxy-benzeneacetic acid 10 g of 4-acetylbenzoic acid, 7 ml of thionyl chloride and 1 ml of dimethyl formamide are dissolved in 100 ml of methylene chloride and boiled for 5 hours. The solution is concentrated, mixed with 11.3 g of methyl 2-methoxy-benzeneacetate in 50 ml methylene chloride, and added dropwise to 40 g of aluminum chloride suspended in 100 ml of methylene chloride. The solution is boiled for 5 hours, poured onto ice water and extracted with chloroform. The chloroform phase is evaporated and hydrolyzed in sodium hydroxide solution. This is acidified and extracted with ethyl acetate. The ethyl acetate solution is concentrated, and crystals thus formed are filtered off. These crystals are dissolved in water - ethanol (3 - 1) and sodium hydroxide. The pH is adjusted to 7, and the solution is treated with active carbon while being subjected to gentle heating. The solution is acidified and cooled. The product is filtered off and the crystals are then again isolated in the same manner.

NMR spectrum and elemental analysis data are consistent with the structure of the title compound. Melting point 235° C.

EXAMPLE 33

2-Hydroxy-5-(2-(4-carboxyphenyl)-1-ethenyl)-benzeneacetic acid 3.14 g of 5-(2-(4-carboxyphenyl)-acetyl)-2-hydroxybenzeneacetic acid are dissolved in 75 ml of tetrahydrofuran and 75 ml of 1M sodium hydroxide. 5.06 g of sodium borohydride are added portionwise. The solution is boiled for 2.5 hours. 150 ml of 1M hydrochloric acid are added. The product is extracted with ethyl acetate. The organic phase is dried and evaporated to dryness. The residue is dissolved in 75 ml of acetic acid, and 16 ml of concentrated sulfuric acid are added. The product crystallizes directly from the solution. It is purified by dissolution in sodium hydroxide followed by acidification with formic acid. This is then repeated once.

NMR spectrum and elemental analysis data are consistent with the structure of the title compound. Melting point >260° C.

EXAMPLE 34

2-Hydroxy-5-(2-phenyl-1-ethenyl)-benzeneacetic acid 0.68 g of 2-hydroxy-5-(2-phenylacetyl)-benzeneacetic acid. 0.95 g of sodium borohydride, 20 ml of tetrahydrofuran and 20 ml of 1M sodium hydroxide are refluxed for 1 hour. The solution is shaken with 100 ml of ether. The aqueous phase is acidified to pH 3 and extracted with 3×50 ml of ether. The ether phases are combined, dried and evaporated to dryness.

The residue is dissolved in 16 ml of acetic acid and 4 ml of concentrated sulfuric acid. The solution is boiled for 15 minutes poured into water, and extracted with ether, whereupon the ether phase is evaporated.

The residue is dissolved in 1M sodium hydroxide. Upon addition of hydrochloric acid the product crystallizes.

NMR spectrum and elemental analysis data are consistent with the structure of the title compound. Melting point 202° C.

EXAMPLE 35

5-(2-Methyl-1-oxo-3-phenyl-2-propenyl)-2-hydroxybenzeneacetic acid 11 g of methyl 5-propanoyl-2-hydroxy-benzeneacetic acid, 10,6 g of benzaldehyde, 150 ml of ethanol and 50 ml of ether saturated with hydrogen chloride are refluxed for 5 days. The solution is poured on to water and extracted with ethyl acetate. The ethyl acetate is evaporated and the residue is hydrolyzed in sodium hydroxide solution. The pH is adjusted to 7 and the solution is washed with ethyl acetate. The aqueous phase is acidified with hydrochloric acid and extracted with ethyl acetate. The ethyl acetate is evaporated, the residue is leached with dichloroethane and recrystallized from 2-butanone/1,2-dichloroethane. NMR spectrum and elemental analysis data are consistent with the structure of the title compound. Melting point 192° C.

EXAMPLE 36

5-[3-(2-Chlorophenyl)-1-oxo-2-propenyl]-2-hydroxybenzeneacetic acid

This synthesis is carried out in a manner analogous to that of Example 16 (b).

NMR spectrum and elemental analysis data are consistent with the structure of the title compound. Melting point 235° C.

EXAMPLE 37

5-[3-(4-Cyanophenyl)-1-oxo-2-propenyl]-2-hydroxybenzeneacetic acid

This synthesis is carried out in a manner analogous to that of Example 16 (b).

NMR spectrum and elemental analysis data are consistent with the structure of the title compound. Melting point 249° C.

EXAMPLE 38

5[3-(4 trifluoromethylphenyl)-1-oxo-2-propenyl]-2-hydroxybenzeneacetic acid monohydrate This synthesis is carried out in a manner analogous to that of Example 16 (b).

NMR spectrum and elemental analysis data are consistent with the structure of the title compound. Melting point >260° C.

EXAMPLE 39

5-[3-(3,4,5-Trimethoxy phenyl)-1-oxo-2-propenyl]-2-hydroxy-benzeneacetic acid

This synthesis is carried out in a manner analogous to that of Example 16 (b).

NMR spectrum and elemental analysis data are consistent with the structure of the title compound. Melting point 210° C.

EXAMPLE 40

5-[3-(3,4-Dimethoxyphenyl)-1-oxo-2-propenyl]-2-hydroxy-benzeneacetic acid

This synthesis is carried out in a manner analogous to that of Example 16 (b).

NMR spectrum and elemental analysis data are consistent with the structure of the title compound. Melting point 225° C.

EXAMPLE 41

5-(2,5-Dichlorobenzoyl)-2-hydroxy-benzeneacetic acid

This synthesis is carried out in a manner analogous to that of Example 10.

NMR spectrum and elemental analysis data are consistent with the structure of the title compound. Melting point 149° C.

EXAMPLE 42

5-(4-Nitrobenzoyl)-2-hydroxy-benzeneacetic acid

This synthesis is carried out in a manner analogous to that of Example 10.

NMR spectrum and elemental analysis data are consistent with the structure of the title compound. Melting point 213° C.

EXAMPLE 43

5-(4-Methylbenzoyl)-2-hydroxy-benzeneacetic acid

This synthesis is carried out in a manner analogous to that of Example 10.

NMR spectrum and elemental analysis data are consistent with the structure of the title compound. Melting point 218° C.

EXAMPLE 44

Sodium 5-benzoyl-2-hydroxy-3,5-dimethyl-benzeneacetate

This synthesis is carried out in a manner analogous to that of Example 10. The product is dissolved in chloroform and shaken with water. Simultaneously sodium hydroxide is added to pH 7,2. The phases were separated and the aqueous phase freeze-dried.

NMR spectrum and elemental analysis data are consistent with the structure of the title compound. Melting point very undefined about 170° C.

EXAMPLE 45

5-(3-Chlorobenzoyl)-2-hydroxy-benzeneacetic acid

This synthesis is carried out in a manner analogous to that of Example 10.

NMR spectrum and elemental analysis data are consistent with the structure of the title compound. Melting point 186° C.

EXAMPLE 46

5-Benzoyl-2-hydroxy-6-methyl-benzeneacetic acid

This synthesis is carried out in a manner analogous to that of Example 10.

NMR spectrum and elemental analysis data are consistent with the structure of the title compound. Melting point 212° C.

EXAMPLE 47

Inhibition of 15-Hydroxy Prostaglandin Dehydrogenase

The efficiency of the compounds as inhibitors of 15-hydroxy-prostaglandin dehydrogenase (PGDH) is demonstrated by in vitro measurements. Radioactive prostaglandin $F_2$ (PGF$_2$) is incubated with cell-free preparations of human placenta (containing PGDH) as desribed by Hoult and Moore, Brithish Journal of Pharmacology Vol. 61 (1977), p. 615. After a suitable incubation period the prostaglandins are extracted and separated chromatographically. The amount of unchanged PGF$_2$ is then compared with the amount of metabolites. The inhibitory effect is evaluated by measurement of the effect in the presence of different amounts of added inhibitor and determination of the concentration (IC$_{50}$) at which 50% inhibition of degradation has been obtained as compared to controls run without inhibitor additions. Very good inhibitors are considered to be those that inhibit PGDH by 50% at a concentration of 10 $\mu$M or less. Good inhibitors are considered to be those that inhibit at a concentration of between 10 and 100 $\mu$M. Also where a compound has to be classified as less good this will often be compensated in actual practice by other valuable properties, such as for instance a low toxicity or particularly suitable pharmacokinetic properties.

The Table below sets forth IC$_{50}$ values for a number of compounds according to the invention. For comparison the Table also gives the IC$_{50}$ value of 5-phenylazo-2-hydroxybenzeneacetic acid which is a known effective PGDH inhibitor described in EP,-A-No. 21229.

Despite their PDGH inhibiting effect of the novel compounds have a relatively low degree of toxicity. In a number of these compounds which have been studied in respect of their toxic effect the acute toxicity values, as measured upon intraperitoneal administration to mice, amount to between 300 and 728 mg/kg.

TABLE

| Compound acc to Example No. | PGDH inhibition IC$_{50}$, $\mu$M |
|---|---|
| 1, 2 | 1.4 |
| 4, 34 | 20 |
| 16 | 12 |
| 14 | 56 |
| 5 | 0.60 |
| 6 | 0.74 |
| 7, 8 | 1.3 |
| 18 | 6.0 |
| 10 | 0.74 |
| 3 | 22 |
| 11 | 0.21 |
| 9 | 42 |
| 17 | 1.4 |
| 33 | 0.40 |
| 15 | 1.7 |
| 20 | 4.9 |
| 21 | 0.58 |
| 12 | 1.3 |
| 25 | 0.38 |
| 29 | 1.3 |
| 30 | 1.9 |
| 32 | 0.63 |
| 5-phenylazo-2-hydroxybenzeneacetic acid | 12 |

We claim:

1. An arylacetic acid derivative having the structure

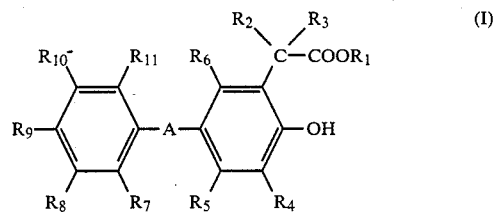

in which

R$_1$ and R$_2$ are hydrogen or lower alkyl, preferably R$_2$ is hydrogen;

R$_3$ is hydrogen, lower alkyl or;

R$_4$, R$_5$ and R$_6$ are hydrogen, halogen, lower alkyl, lower alkoxy, cyano, carboxy or nitro; at least one of the groups R$_4$ to R$_6$ being hydrogen;

R$_7$ to R$_{11}$ are hydrogen, halogen, cyano, lower alkyl, trifluoromethyl, lower alkoxy, hydroxy, lower acyl, lower alkxycarbonyl, N,N,-diloweralkylaminocarbonyl or N,N-loweralkylene-aminocarbonyl; and R$_8$ to R$_{10}$ may in addition be carboxy; at least two of R$_7$ to R$_{11}$ always being hydrogen; preferably R$_7$ and R$_{11}$ are hydrogen, halogen, cyano, lower alkyl, trifluoromethyl, lower alkoxy, hydroxy or lower acyl; and —A— is —CO—, —CH$_2$—CO—, —CH=CH—, —CH=CH—CO— or corresponding groups in which a hydrogen atom is replaced by a lower alkyl group; or salts thereof in cases where the compound comprises at least one carboxy group; or corresponding lactones in cases where R$_1$ is H.

2. An arylacetic acid derivative according to claim 1 in which $R_2$ is hydrogen, or a corresponding carboxylic acid salt.

3. An arylacetic acid derivative according to claim 1 in which $R_3$ - $R_6$ are hydrogen.

4. An arylacetic acid derivative according to claim 1 which is a lactone of the corresponding acid where $R_1$ is H.

5. An arylacetic acid derivative according to claim 1 in which at least one of $R_8$, $R_9$ and $R_{10}$ is carboxy.

6. An arylacetic acid derivative according to claim 1 in which $R_4=R_5=R_6=R_7=R_{11}=$ hydrogen.

7. An arylacetic acid derivative according to claim 1 in which A is —CO—.

8. An arylacetic acid derivative according to claim 1 in which A is —CH=CH—.

9. An arylacetic acid derivative according to claim 1 in which A is —CH$_2$—CO—.

10. An arylacetic acid derivative according to claim 1 in which A is —CH=CH—CO—.

11. A pharmaceutical composition containing a therapeutically active amount of a compound according to claim 1.

* * * * *